(12) United States Patent
Wartig

(10) Patent No.: US 10,808,101 B2
(45) Date of Patent: Oct. 20, 2020

(54) COMPOSITION FOR HYDROLYTIC STABILIZATION OF POLYESTER

(71) Applicant: CLARIANT PLASTICS & COATINGS LTD, Muttenz (CH)

(72) Inventor: Karen-Alessa Wartig, Hamburg (DE)

(73) Assignee: Clariant Plastics & Coatings Ltd, Muttenz (CH)

( * ) Notice: Subject to any disclaimer, the term of this patent is extended or adjusted under 35 U.S.C. 154(b) by 0 days.

(21) Appl. No.: 16/098,467

(22) PCT Filed: Apr. 26, 2017

(86) PCT No.: PCT/EP2017/059848
§ 371 (c)(1),
(2) Date: Nov. 2, 2018

(87) PCT Pub. No.: WO2017/190993
PCT Pub. Date: Nov. 9, 2017

(65) Prior Publication Data
US 2019/0153195 A1    May 23, 2019

(30) Foreign Application Priority Data
May 4, 2016  (EP) .................................... 16168305

(51) Int. Cl.
| | | |
|---|---|---|
| C08K 5/12 | (2006.01) |
| C08J 3/22 | (2006.01) |
| C08J 5/18 | (2006.01) |
| C07C 69/82 | (2006.01) |
| C08K 5/3492 | (2006.01) |
| C08L 67/02 | (2006.01) |

(52) U.S. Cl.
CPC .............. C08K 5/12 (2013.01); C07C 69/82 (2013.01); C08J 3/226 (2013.01); C08J 5/18 (2013.01); C08K 5/3492 (2013.01); C08L 67/02 (2013.01); C08J 2367/00 (2013.01); C08J 2367/02 (2013.01); C08J 2467/02 (2013.01); C08J 2469/00 (2013.01); C08K 2201/014 (2013.01); C08L 2201/08 (2013.01); C08L 2203/16 (2013.01); C08L 2205/025 (2013.01); C08L 2205/035 (2013.01); C08L 2310/00 (2013.01)

(58) Field of Classification Search
CPC ........ C08K 5/12; C08K 5/3492; C07C 69/82; C08L 67/02; C08J 3/226; C08J 5/18
See application file for complete search history.

(56) References Cited

U.S. PATENT DOCUMENTS

| | | |
|---|---|---|
| 3,657,191 A | 4/1972 | Titzmann et al. |
| 5,885,709 A | 3/1999 | Wick et al. |
| 2006/0057409 A1 | 3/2006 | Kliesch et al. |
| 2010/0233406 A1* | 9/2010 | Andrews ............ C08L 67/02 428/36.92 |
| 2011/0305913 A1 | 12/2011 | Hinton et al. |
| 2013/0137789 A1 | 5/2013 | Olsen et al. |
| 2013/0320594 A1* | 12/2013 | Bechard ............ B07C 5/34 264/344 |

FOREIGN PATENT DOCUMENTS

| | | |
|---|---|---|
| CH | 621135 A5 | 1/1981 |
| EP | 0 292 251 A2 | 11/1988 |
| EP | 0 838 500 A2 | 4/1998 |

OTHER PUBLICATIONS

International Search Report and Written Opinion dated Jul. 27, 2017, issued in corresponding International Patent Application No. PCT/EP2017/059848.

* cited by examiner

*Primary Examiner* — John E Uselding
(74) *Attorney, Agent, or Firm* — Morgan, Lewis & Bockius LLP

(57) ABSTRACT

The invention relates to the use of at least one compound of the formula (1) wherein $R_1$ and $R_2$ are the same or different and denote a $C_1$-$C_{10}$-alkyl as a hydrolysis stabilizer in polyester materials.

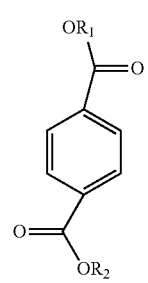

(1)

13 Claims, No Drawings

COMPOSITION FOR HYDROLYTIC STABILIZATION OF POLYESTER

The present invention relates to hydrolysis-resistant polyester films.

Polyester films are well known. However, a disadvantage of unstabilized polyester films is their susceptibility to hydrolysis, especially at temperatures above the glass transition temperature of the particular polyester. Susceptibility to hydrolysis is the property of the polyester to hydrolytically degrade under moisture conditions, which can be seen for example in a reduction in the IV value. This is a limiting factor for the use of polyester films, particularly in applications with high temperature stress, such as in film capacitors, cable sheathing, ribbon cables, motor protection films, battery films, flooring films, window films, photovoltaic back sheets but also in long-term applications such as in glazing and outdoor applications.

Particularly pronounced susceptibility to hydrolysis is observed in aliphatic polyesters, but also with aromatic polyesters such as PBT and PET. When the hydrolysis tendency of PET is too large for the application, one has to resort to hydrolysis-stable PEN or even to other polymers such as polyether or polyimides. However, they are significantly more expensive than PET and therefore disadvantageous for economic reasons.

Therefore, it has been proposed to improve the hydrolytic stability of polyester films by incorporating hydrolysis stabilizers.

Hydrolysis resistant polyester raw materials, which are obtained by using carbodiimides, are known (U.S. Pat. No. 5,885,709, EP-A-0838500, CH-A-621 135). Films prepared from such polymers tend, however, both in manufacturing and in the later use to outgas isocyanates which are irritant to the mucous membrane, or set free other harmful byproducts and degradation products. Hydrolysis stabilizers based on epoxy groups also give hydrolysis stabilization and are described for example in EP-A-0 292 251 or U.S. Pat. No. 3,657,191. However, these compounds are based on the generation of oxirane rings by means of epichlorohydrin, but display a tendency for cleaving low molecular weight toxic compounds, so that similar problems as associated with the use of carbodiimides arise. Furthermore, their incorporation into the polyester matrix is insufficient, leading to long reaction times and oriented polyester films in high clouding.

Moreover, known hydrolysis stabilizers such as carbodiimides and other substances such as those described in EP-A-0 292 251 have the disadvantage that they sometimes lead to strong increase in molecular weight (viscosity increase) in the polymer during extrusion and thus make the extrusion process unstable and difficult to control.

It is therefore an object of the present invention to provide a hydrolysis-resistant polyester raw material available which avoids the disadvantages of the prior art described.

The object is surprisingly achieved by a polyester article, preferably a film, which contains a hydrolysis stabilizer based on a terephthalic acid ester.

The present invention is directed to the use of at least one compound of the formula (1)

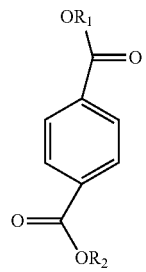

wherein
$R_1$ and $R_2$ are the same or different and denote a $C_1$-$C_{10}$-alkyl, preferably $C_1$-$C_6$-alkyl, more preferably $C_1$-$C_4$-alkyl, most preferably $C_1$-$C_2$-alkyl, as a hydrolysis stabilizer in polyester materials.

Examples for compounds of the formula (1) are dimethylterephthalat, diethylterephthalat, dipropylterephthalat, dibutylterephthalat, dipentylterephthalat, dihexylterephthalat, diheptylterephthalat, dioctylterephthalat, dinonylterephthalat or didecylterephthalat.

The preferred chain extender is dimethylterephthalat (DMT) of formula (2)

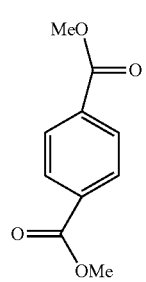

This molecule can be manufactured by oxidation of the methyl groups on p-xylene and reaction with methanol giving the methyl ester, dimethyl terephthalate. The proportion of the hydrolysis stabilizer is preferably in the range from 0.1 to 20.0 wt.-%, more preferably from 1.0 to 10.0 wt.-%, and particularly preferably 1.5 to 5 wt.-%, based on the weight of the polyester.

If incorporated in a masterbatch, the proportion of the hydrolysis stabilizer is generally from 0.1 to 50.0 wt.-%, preferably 1.0 to 20.0 wt.-%, each based on the total weight of the masterbatch.

Suitable polyesters are, for example, polyethylene terephthalate (PET), polyethylene naphthalate (PEN), polybutylene terephthalate (PBT), polytrimethylene terephthalate (PTT), dibenzoyl polyethylene terephthalate (PETBB), dibenzoyl polybutylene terephthalate (PBTBB), dibenzoyl polyethylene naphthalate (PENBB) or mixtures thereof. Preferred are PET, PBT, PEN and PTT, and mixtures and co-polyesters thereof.

Suitable polyesters are also aliphatic polyesters such as polyhydroxybutyrate (PHB) and its copolymer with polyhydroxyvalerate (PHV), polyhydroxybutyrate-valerate (PHBV), poly (ε-caprolactone) (PCL), SP 3/6, 4/6 SP (consisting of 1, 3-propanediol/adipate or 1,4-butanediol/adipate), polycaprolactam or generally adipic-acid polyester and the esters of other aliphatic carboxylic acids.

The polyester used in the invention may further contain inorganic or organic particles, which are needed for adjusting the surface topography or optical properties and are called polyester composition hereinafter. The amount of the particlesis dependent on the use and their particle size. The latter is generally in the range of 0.01 to 30.0, preferably 0.1 to 5.0, and especially 0.3 to 3.0 microns.

Suitable compounds for obtaining roughness are e.g. calcium carbonate, barium sulphate, apatite, silicon dioxide, titanium dioxide, aluminum oxide, crosslinked polystyrene, crosslinked PMMA, zeolites, and other silicates such as aluminum silicates. These compounds are generally used in amounts of 0.05 to 5 wt.-%, preferably 0.1 to 0.6 wt.-%, (based on the total weight of the polyester composition).

Apart from the before mentioned additives, the polyester composition may additionally contain other components such as flame retardants and/or radical scavengers and/or other polymers, such as polyetherimides, pigments and dyes, stabilizers, antioxidants, antibacterial agents, thermostabilizers, light stabilizers, neutralizers, antistatic agents, antiblocking agents, optical brighteners, heavy metal inactivation agents, hydrophobic agents, peroxides, water scavengers, acid scavengers, hydrotalcites, elastomers, impact modifiers, laser marking additives, processing aids, and mixtures thereof.

The hydrolysis stabilizer of formula (1) is preferably added by way of masterbatch technology. For this purpose, the hydrolysis stabilizer is first dispersed in a carrier material. Suitable support materials are the polyester itself, e.g. polyethylene terephthalate, or other polymers which are compatible with the respective polyester. Depending on the carrier resin the masterbatch can be solid or liquid, a solid being preferred. After the addition of the masterbatch into the polyester material, the components of the masterbatch melt during extrusion and are dissolved or finely dispersed in the polyester. As the hydrolysis stabilizer is physically homogeneously dispersed in the carrier, while the masterbatch is mixed with the polyester, the potential for localized higher concentrations of hydrolysis stabilizer is minimized. Furthermore, when introduced into a molding apparatus, a premature reaction of the hydrolysis stabilizer within the let down polymer is prevented by increasing the time required to melt the concentrate. This delayed reaction time permits the hydrolysis stabilizer to be fully dispersed throughout the polymer.

The hydrolysis stabilizer of formula (1) can be incorporated into the polyester material to be stabilized as follows:

The carrier material of the masterbatch to be produced and the hydrolysis stabilizer are fed into an extruder, preferably a twin-screw extruder, melted, mixed and then extruded through a perforated die, quenched and granulated. Preferred is a method in which the polymer is first melted in an extruder and after degassing the hydrolysis stabilizer is metered directly into the melt.

The hydrolysis stabilized polyester material is expediently processed into a polymeric article, e.g. sheets, films, containers or fibers. Sheets and films are particularly preferred.

Advantageously, the hydrolysis stabilized polyester articles, e.g. films, contain further customary polymer stabilizers such as a radical scavenger, light stabilizers or heat stabilizers, advantageously in amounts of from 50 to 15,000 ppm, preferably 100 to 5,000 ppm, more preferably 300 to 1000 ppm, based on the total weight of the article. The polymer stabilizers added can be selected from the group of the primary stabilizers, such as sterically hindered phenols or secondary aromatic amines or the group of secondary stabilizers such as thioethers, and phosphonites, and zinc dibuthyl-dithio-carbamate or mixtures of primary and secondary stabilizers. Preferred are phenolic stabilizers. Particularly preferred among the phenolic stabilizers are sterically hindered phenols, thiobisphenols, alkylidenebisphenols, alkyl phenols, hydroxybenzyl compounds, acyl-amino and hydroxyphenylpropionates.

Also UV-absorbers, based on benzotriazoles, like Tinuvin 1577, Tinuvin 1600, Tinuvin 360, Tinuvin 234, Cyasob 3638, Cyasorb 1164, are advantageously used in films for outdoor applications. These additives might be added in the range from 0.1 to 20.0 wt.-%, preferably from 1.0 to 10.0 wt.-%, and particularly preferably 1.5 to 5 wt.-%, based on the total weight of the film.

Apart from the addition of the hydrolysis stabilizer in form of a masterbatch, the hydrolysis stabilizer may be added directly during the production of the polyester article, e.g. film. Particularly good results are obtained when twin-screw extruders are used and the hydrolysis stabilizer is metered directly into the melt in the respective extruder.

Films can be prepared by conventional extrusion processes for producing monolayer and multilayer films. The hydrolysis stabilizer is preferably present in all layers, embodiments are also possible, in which not all layers are modified with the hydrolysis stabilizer.

Commonly, the respective melts are extruded through a flat-film die, the resultant film for solidification on one or more roller/s (cooling roll) is withdrawn as a substantially amorphous prefilm, and quenched, the film is then reheated and biaxially stretched (oriented) and the biaxially stretched film is heat-set. The biaxial stretching is performed sequentially in machine direction (=MD) and then transversely, perpendicular to the machine direction (=TD). This leads to an orientation of the molecular chains.

The temperature at which the orientation is carried out can vary over a relatively wide range and depends on the desired properties of the film. The first longitudinal stretching can optionally be carried out simultaneously with the transverse stretching (simultaneous stretching).

Film produced in this manner has a much lower tendency to hydrolyze in both room temperature and at temperatures up to 210° C. than an unmodified polyester film. The stabilization is largely independent of the film thickness and the temperature.

It was particularly surprising that despite the good long-term hydrolysis, no undesired viscosity increase in the extruder during film production occurs and no increased gel or speck level was observed.

Films, which are stabilized by means of the hydrolysis stabilizer of formula (1) are ideal for the production of products containing polyester films which should have a long life (greater than 1 year), and are employed in applications where higher temperatures (above 80° C.) and high humidity are present.

The stabilizers of formula (1) are especially useful for the production of film capacitors (preferred thickness range from 0.3 to 12 microns). For the manufacture of capacitors, it has proved to be advantageous when the films have a longitudinal shrinkage of less than 4% and a transverse shrinkage of less than 1% at 200° C., as it particularly well suited for the production of SMD capacitors.

Another application is for ribbon cables in automobiles.

In the following embodiments, the measurement of individual properties are in accordance with approved standard methods. Percentages are weight percent unless indicated otherwise.

Measurement Methods

Pressure Cooker Test PCT

This kind of test provides information about hydrolysis resistivity as fast track. Samples were cut before autoclaving and stored at 120° C. and 2 bar (abs) for 0, 40, 50 h. For each test, five test samples were measured.

Damp Heat Test DHT

This kind of test provides information about hydrolysis resistivity as long-term process. Samples were cut before autoclaving and stored at 85° C. and normal pressure up to 5000 h, after each 500 h test results were measured.

Tensile Testing

The tensile test was processed with an aluminum clamp of 100 mm compliant with ISO 527-1/2 to obtain elongation at break and tensile strength. The results are the averaged values of five measurements.

Testing speed:

$\varepsilon < 0.25\%$: 1 mm/min $\varepsilon > 0.25\%$: 100 mm/min

Elongation at break retention is measured to receive an indication of embrittlement of the film, after x h autoclaving:

$$= \frac{\text{Elongation at break after x h autoclaving}}{\text{Elongation at break after 0 h autoclaving}}$$

Intrinsic Viscosity (I.V.)

The measurement of the intrinsic viscosity (I.V.) was used to measure the molecular weight of the polymer, as the intrinsic viscosity is a unique function of the molecular weight of a polymer. The I.V. was detected by using a Davenport viscosimeter for melt viscosity measurements, e.g. for PET, in the molten state extruded through a calibrated die using high pressure nitrogen gas.

Standard viscosity (S.V.)

The standard viscosity S.V. is—based on DIN 53726. By measuring the relative viscosity $\eta_{rel}$ of a 1% solution in dichloroacetic acid (DCA) in an Ubbelohde viscometer at 25° C. The S.V. value is defined as follows:

$$S.V. = (\eta_{rel} - 1) \cdot 1000 \quad S.V. = (\eta_{rel} - 0.1) \times 1000$$

EXAMPLES

The following materials are used:

PET1: (XPURE 4004, Invista, I.V. 0.63)

PET2: regranulat RT4027 (Invista/Erema)

PET3: RAMAPET R 180 GR BB (Indorama Plastics)

PC (Polycarbonate): (Trirex 3022PJ(01) Entec)

Hydrolysis stabilizator: DMT (dimethylterephthalat)

UV-Absorber: 2-(4,6-Diphenyl-1,3,5-triazin-2-yl)-5-hexyloxy-phenol (TINUVIN 1577 ED, BASF)

Two Masterbatches (MB) were produced by using a twin-screw extruder Leistritz MASS technology (27 mm/40D). MBHS contains 10% of DMT on PC for the hydrolysis stabilization. MBUV contains 15% of the UV-absorber Tinuvin 1577 on PET3.

Example 1

A three layer film was produced with a structure of ABA. The composition of the core layer B consists of 53% PET1, 15% PET 2, 2% MBHS, 30% MBUV. The outer layers A consists of 67% PET1, 3% MBHS, 30% MBUV. The used PET was predried at 100-170° C. The main extruder was equipped with vacuum ~10 mbar. The coextruder was equipped with vacuum~20 mbar.

The extrusion temperatures of the different zones are displayed in Table 1.

TABLE 1

| Extrusion Temperatures in ° C.: | | | | | | | | |
|---|---|---|---|---|---|---|---|---|
| Zone 1 | Zone 2 | Zone 3 | Zone 4 | Zone 5 | Zone 6 | Zone 7 | Zone 8 | Zone 9 |
| 100 | 102 | 104/105 | 106 | 120/130 | 210 | 210/215 | 220 | 200/190 |

The molten polymer was discharged from a nozzle of a draw roller. The film was stretched by a factor of 3.0 in the machine direction and stretched in a cross-stretching by a factor of 3.4. Subsequently, the film was heat set at 225° C. and relaxed in the transverse direction by 3% at temperatures of 220-180° C. The final film thickness was 50 microns.

Example 2 (Comparative)

A three layer film was produced with a structure of ABA. The composition of the core layer B consists of 45% PET1, 25% PET 2, 30% MBUV. The outer layers A consists of 70% PET1, 30% MBUV. The used PET was predried at 100-170° C. The main extruder was equipped with vacuum ~10 mbar. The coextruder was equipped with vacuum~20 mbar.

The extrusion temperatures of the different zones are displayed in Table 2.

TABLE 2

| Extrusion Temperatures in ° C.: | | | | | | | | |
|---|---|---|---|---|---|---|---|---|
| Zone 1 | Zone 2 | Zone 3 | Zone 4 | Zone 5 | Zone 6 | Zone 7 | Zone 8 | Zone 9 |
| 100 | 102 | 104/105 | 106 | 120/130 | 210 | 210/215 | 220 | 200/190 |

The molten polymer was discharged from a nozzle of a draw roller. The film was stretched by a factor of 3.0 in the machine direction and stretched in a cross-stretching by a factor of 3.4. Subsequently, the film was heat set at 225° C. and relaxed in the transverse direction by 3% at temperatures of 220-180° C. The final film thickness was 50 microns.

Test Results

TABLE 3

| Test | Example 1 | Example 2 comp. |
|---|---|---|
| Pressure Cooker Test = | 78% after 40 h | 76% after 40 h |
| Elongation at break retention after autoclavation (120° C./2 bar abs) | 69% after 50 h 69% after 60 h | 42% after 50 h |
| Damp Heat Test | 71% after 2000 h | 43% after 2000 h |
| Elongation at break retention after conditioning (85% rH/85° C.) | 52% after 2500 h | 1% after 2500 h |
| Intrinsic melt Viscosity (I.V.) | 0.621 | 0.527 |
| Standard Viscosity (S.V.) | 0.628 | 0.608 |

The test results of example 1, which contain the anti-hydrolysis-additive convinces in all tests, which simulate hydrolysis degradation of polymer. In the pressure cooker test the film stayed significantly longer stabile than the film without anti-hydrolysis-additive. Also in the damp heat test the material equipped with anti-hydrolysis-additive resisted significantly longer than the non-equipped film. Also the measurement of the melt viscosity and the standard viscosity show the more stabilized material is the one which was equipped with the anti-hydrolysis-additive. All films of Example 1 display a high UV stability.

The invention claimed is:

1. A method of stabilization of polyester materials against hydrolysis said method being characterized by adding at least one compound of the formula (1)

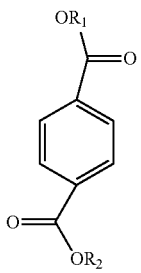

(1)

wherein

R$_1$ and R$_2$ are the same or different and denote a C$_1$-C$_{10}$-alkyl, as a hydrolysis stabilizer in said polyester materials, and wherein the compound of formula (1) is in a proportion of from 0.1 to 20.0 wt.-%, based on the weight of a proportion of the stabilized polyester materials.

2. The method as claimed in claim 1, wherein the compounds of the formula (1) are dimethylterephthalate, diethylterephthalate, dipropylterephthalate, dibutyl-terephthalate, dipentylterephthalate, dihexylterephthalate, diheptylterephthalate, dioctylterephthalate, dinonylterephthalate or didecylterephthalate.

3. The method as claimed in claim 1, wherein the compound of formula (1) is dimethylterephthalate.

4. The method as claimed in claim 1, wherein the polyester in the polyester materials is polyethylene terephthalate, polyethylene naphthalate, polybutylene terephthalate, polytrimethylene terephthalate, dibenzoyl polyethylene terephthalate, dibenzoyl polybutylene terephthalate, dibenzoyl polyethylene naphthalate or mixtures thereof.

5. The method as claimed in claim 1, wherein the polyester in the polyester materials is polyethylene terephthalate, polybutylene terephthalate, polyethylene naphthalate and polytrimethylene terephthalate, and mixtures and co-polyesters thereof.

6. The method as claimed in claim 1, wherein the polyester in the polyester materials are aliphatic polyesters selected from the group consisting of polyhydroxybutyrate and its copolymer with polyhydroxyvalerate, polyhydroxybutyrate-valerate, poly (ε-caprolactone).

7. The method as claimed in claim 1, further comprising forming the polyester materials in to a stretched film.

8. The method as claimed in claim 1, wherein the proportion of the compound of formula (1) is from 1.0 to 10.0 wt.-%, based on the weight of the stabilized polyester material.

9. The method as claimed in claim 1, wherein the proportion of the compound of formula (1) is from 1.5 to 5.0 wt.-%, based on the weight of the stabilized polyester material.

10. The method as claimed in claim 1, wherein the compound of formula (1) is added in combination with further additives selected from the group consisting of radical scavengers, light stabilizers, heat stabilizers, flame retardants, pigments, dyes, antioxidants, antibacterial agents, neutralizers, antistatic agents, antiblocking agents, optical brighteners, heavy metal inactivation agents, hydrophobic agents, peroxides, water scavengers, acid scavengers, hydrotalcites, elastomers, impact modifiers, laser marking additives, processing aids, and mixtures thereof.

11. The method as claimed in claim 1, wherein the compound of formula (1) is added in combination with UV-absorbers.

12. The method as claimed in claim 1, further comprising dispersing the compound of formula (1) in a carrier material to form a masterbatch and adding the masterbatch to said polyester materials.

13. The method as claimed in claim 1, wherein the polyester material is in the form of a film or a sheet.

* * * * *